United States Patent [19]

Wang

[11] Patent Number: 5,795,568
[45] Date of Patent: Aug. 18, 1998

[54] METHOD OF TREATING INFECTIOUS DISEASE WITH GM-CSF

[75] Inventor: Elizabeth A. Wang, Carlisle, Mass.

[73] Assignee: Novartis Corporation, Basel, Switzerland

[21] Appl. No.: 469,530

[22] Filed: Jun. 6, 1995

Related U.S. Application Data

[62] Division of Ser. No. 344,809, Nov. 23, 1994, which is a continuation of Ser. No. 183,099, Jan. 14, 1994, abandoned, which is a continuation of Ser. No. 23,146, Feb. 24, 1993, abandoned, which is a continuation of Ser. No. 752,250, Aug. 28, 1991, abandoned, which is a continuation of Ser. No. 657,350, Feb. 15, 1991, abandoned, which is a continuation of Ser. No. 652,742, Sep. 19, 1984, abandoned.

[51] Int. Cl.$^6$ .......................... A61K 38/19; C07K 14/535
[52] U.S. Cl. ................. 424/85.1; 424/184.1; 424/198.1; 514/2; 514/8; 514/12; 514/885
[58] Field of Search ................. 514/2, 8, 12, 885; 424/84, 85.1, 85.2, 184.1, 198.1; 530/351

[56] References Cited

U.S. PATENT DOCUMENTS

| | | | |
|---|---|---|---|
| 5,078,996 | 1/1992 | Conlon, III et al. | 424/85.1 |
| 5,147,799 | 9/1992 | Bursuker et al. | 435/240.1 |
| 5,162,111 | 11/1992 | Grabstein et al. | 424/85.1 |

OTHER PUBLICATIONS

Yunis, et al., FEBS Letters, 1978, 90:279–82.
Wu, et al. J. Biol. Chem., 1979, 254:6226–28.
Gasson, et al. Science, 1984, 226:1339–1342.
Fojo, et al., Biochemistry, 1978, 17:3109–16.
Lusis, et al., Blood, 1981, 57:13–21.
Nicola, et al., Blood, 1979, 54:614–27.
Fojo, et al., Biophys. Acts., 1977, 494:92–99.
Price, et al., Biochem. J., 1975, 148:209–17.
Metcalf, The Hemopoietic Colony Stimulating Factors, Elsevier (1984), pp. 81–84, 215–227, 309–329.
Wing et al. (1982) J. Clin. Investigation vol. 69 pp. 270–276.
Lusis et al. (1980) Proc. Natl. Acad. Sci. U.S.A. vol. 77, No. 9, pp. 5346–5350.

*Primary Examiner*—John Ulm
*Assistant Examiner*—Prema Mertz
*Attorney, Agent, or Firm*—Fitzpatrick, Cella, Harper & Scinto

[57] ABSTRACT

A method for purifying CSF protein is described. The method comprises: precipitating the protein with ammonium sulfate at 80% saturation to form a pellet containing the CSF protein; resuspending the pellet in a buffered solution at a pH in the range of about 6 to about 8; applying the buffered solution containing CSF to a chromatographic columns eluting with the buffered solution containing sodium chloride and collecting the fractions having CSF activity; pooling the active fractions, applying them to a C4 reverse phase column and eluting with a 0 to 90% acetonitrile gradient to collect the active fractions. The purified CSF protein has a specific activity of at least about $1 \times 10^7$ units per mg of protein and preferably at least about $4 \times 10^7$ units per mg of protein when assayed using the human bone marrow assay.

6 Claims, 2 Drawing Sheets

```
                10                        30                           45
GAATTCCGCT  GGAGG ATG TGG CTG CAG AGC CTG CTG CTC TTG GGC ACT GTG GCC TGC
                  MET Trp Leu Gln Ser Leu Leu Leu Leu Gly Thr Val Ala Cys 60                   75                       90                    105
AGC ATC TCT GCA CCC GCC CGC TCG CCC AGC CCC AGC ACG CAG CCC TGG GAG CAT
Ser Ile Ser Ala Pro Ala Arg Ser Pro Ser Pro Ser Thr Gln Pro Trp Glu His 120                     135                    150                     165
GTG AAT GCC ATC CAG GAG GCC CGG CGT CTC CTG AAC CTG AGT AGA GAC ACT GCT
Val Asn Ala Ile Gln Glu Ala Arg Arg Leu Leu Asn Leu Ser Arg Asp Thr Ala 180                       195                     210
GCT GAG ATG AAT GAA ACA GTA GAA GTC ATC TCA GAA ATG TTT GAC CTC CAG GAG
Ala Glu MET Asn Glu Thr Val Glu Val Ile Ser Glu MET Phe Asp Leu Gln Glu 225                     240                     255                    270
CCG TCC TGC CTA CAG ACC CGC CTG GAG CTG TAC AAG CAG GGC CTG CGG GGC AGC
Pro Ser Cys Leu Gln Thr Arg Leu Glu Leu Tyr Lys Gln Gly Leu Arg Gly Ser 285                     300                     315
CTC ACC AAG CTC AAG GGC CCC TTG ACC ATG ATG GCC AGC CAC TAC AAG CAG CAC
Leu Thr Lys Leu Lys Gly Pro Leu Thr MET MET Ala Ser His Tyr Lys Gln His 330                    345                     360                     375
TGC CCT CCA ACC CCG GAA ACT TCC TGT GCA ACC CAG ACT ATC ACC TTT GAA AGT
Cys Pro Pro Thr Pro Glu Thr Ser Cys Ala Thr Gln Thr Ile Thr Phe Glu Ser 390                     405                     420                    435
TTC AAA GAG AAC CTG AAG GAC TTT TTG CTT GTC ATC CCC TTT GAC TGC TGG GAG
Phe Lys Glu Asn Leu Lys Asp Phe Leu Leu Val Ile Pro Phe Asp Cys Trp Glu 450        460        470        480        490        500
CCA GTC CAG GAG    TGA GACCGGCCAG ATGAGGCTGG CCAAGCCGGG GAGCTGCTCT CTCATGAAAC
Pro Val Gln Glu 510        520        530        540        550        560        570
AAGAGCTAGA AACTCAGGAT GGTCATCTTG GAGGGACCAA GGGGTGGGCC ACAGCATGGT GGGAGTGGCC 580        590        600        610        620        630        640
TGGACCTGCC CTGGGCCACA CTGACCCTGA TACAGGCATG GCAGAAGAAT GGGAATATTT TATACTGACA 650        660        670        680        690        700        710
GAAATCAGTA ATATTTATAT ATTTATATTT TTAAAATATT TATTTATTTA TTTATTTAAG TTCATATTCC 720        730        740        750        760        770        780
ATATTTATTC AAGATGTTTT ACCGTAATAA TTATTATTAA AAATATGCTT CTAAAAAAAA AAAAAAAAAA
```

FIG. 1

METHOD OF TREATING INFECTIOUS DISEASE WITH GM-CSF

This is a division of application Ser. No. 08/344,806, filed Nov. 23, 1994, which in turn is a continuation of application Ser. No. 08/183,099, filed Jan. 14, 1994, now abandoned, which in turn is a continuation of application Ser. No. 08/023,146, filed Feb. 24, 1993, now abandoned, which in turn is a continuation of application Ser. No. 07/752,250, filed Aug. 28, 1991, now abandoned, which in turn is a continuation of application Ser. No. 07/657,350, filed Feb. 15, 1991, now abandoned, which in turn is a continuation of application Ser. No. 06/652,742, filed Sep. 19, 1994, now abandoned.

FIELD OF THE INVENTION

This invention relates to the purification of a protein having the ability to stimulate the growth and differentiation of primate hematopoietic progenitor cells, i.e. colony stimulating factor (CSF) protein, particularly a method for purifying CSF protein and substantially pure CSF protein obtained thereby.

BACKGROUND OF THE INVENTION

The many different cell types found in blood are all derived from pluripotent hematopoietic stem cells. Stem cells perform two functions: (1) they reproduce themselves, thereby maintaining a stem cell population in the body and (2) they provide progeny cells committed to differentiate into any of the imature blood cell types. The cell which is committed to differentiate along a particular hematopoietic pathway is termed a progenitor cell. Progenitor cells For T lymphocytes, B lymphocytes, granulocytes, macrophages, red blood cells, platelets, and eosinophils, as well as earlier progenitors which can individually give rise to several of the mature cell types, have been studied experimentally both n vivo and in vitro (Dexter, T. M. 1983 J. Pathology 141 415–433). it has been determined in vitro that proliferation and/or differentiation of each progenitor cell type depends upon specific "factors" which have been obtained from various sources. For example, the later progenitors of red blood cells require for their proliferation and differentiation a factor called erythropoietin. The factors required for survival, proliferation and differentiation of the progenitor cells committed to form mature neutrophilic granulocytes and macrophages are called colony stimulating factors (CSFs).

CSF activity has been studied extensively in the mouse. Most adult mouse organs produce CSF activity. However, compositions containing CSF activity that have been obtained from various tissues and by various methods appear to differ in their biochemical characteristics. Thus, the structural relationships between the different factors remain unknown. Furthermore, CSF I activity appears to act at more than one step of granulocyte and macrophage development, and again it has been uncertain whether a single factor is responsible for all of the observed activities or whether a different factor acts at each step-(Burgess, A. and Metcalf, D. 1980 Blood 56 947–957).

Human CSF activity has been obtained from placenta, certain fetal tissues, macrophages, and stimulated T cells. A line of T cells (Mo) that produces one or more potent CSF activities was established from a patient with a T cell variant of hairy cell leukemia (leukaemic reticuloendotheliosis) (Golde et al 1978 Blood 52 1068–1072).

The ability of CSF activity to stimulate granulocyte and macrophage production indicates that pharmaceutical compositions having CSF activity are clinically useful in situations where increased production of these (myeloid) cell types is required. Indeed, several patients with extremely high levels of apparently normal circulating granulocytes have been shown to have tumors which over-produce CSFS. In one case, upon surgical removal of the tumor, the granulocyte count rapidly declined towards a normal level, strongly suggesting that CSFs may be useful in regulating the numbers of circulating granulocytes. (Hocking, W. r Goodman, J., and Golde, D. Blood 61 600 (1983)). In particular, CSF compositions are useful clinically for the treatment of myelo-suppress-on caused by chemotherapeutical or irradiation treatment of cancer. In addition, CSF compositions are useful in treating severe infections because CSF can increase and or activate the number of granulocytes and/or monocytes.

Biological and biochemical characterization of compositions having CSF activity, and study of these compositions in the clinical setting have been hampered to date by the scarcity and impurity of human and/or other primate CSF compositions. It can be appreciated that it would be desirable to identify the proteins or proteins responsible for CSF activity. Furthermore, it would be desirable to have a primate, preferably human, source of such CSF activity that could readily supply these proteins in quantities and purity sufficient for biological and biochemical, characterization and for use as therapeutic agents. The Mo cell line has been used both as a starting material for purifying human CSFs and for identifying the corresponding messenger RNAs. However even with this relatively good source of CSF activity, it has proved to be extremely difficult to isolate protein having sufficient purity for structural studies. Thus, new and better methods for purifying CSFs are desired.

SUMMARY OF THE INVENTION

The present invention overcomes the problems of the prior art and provides a method for purifying protein having CSF activity. CSF protein in accord with the present invention, has a specific activity of at least about $1 \times 10^7$ units per mg of protein and preferably at least about $4 \times 10^7$ units per mg of protein when assayed using the human bone marrow assay.

In accord with the present invention, a method for purifying, CSF protein comprises: precipitating the protein with ammonium sulfate at 80% saturation to form a pellet containing the CSF protein; resuspending the pellet in a buffered solution at a pH in the range of about 6 to about 8; applying the buffered solution containing CSF to a chromatographic column, eluting with the buffered solution containing sodium chloride and collecting the fractions having CSF activity; pooling the active fractions, applying them to a C4 reverse phase column and eluting with a 0 to 90% acetonitrile gradient to collect the active fractions.

The CSF proteins of this invention are growth and differentiation hormones for the cells of the myeloid system. They are useful clinically for the treatment of myelo-suppression especially (sympotomatic) granulocyto-penia following chemotherapeutical or irradiation treatment of cancer.

BRIEF DESCRIPTION OF THE DRAWINGS

FIG. 1 illustrates the DNA sequence that codes for a CSF protein.

DETAILED DESCRIPTION OF THE INVENTION

Figure 2:
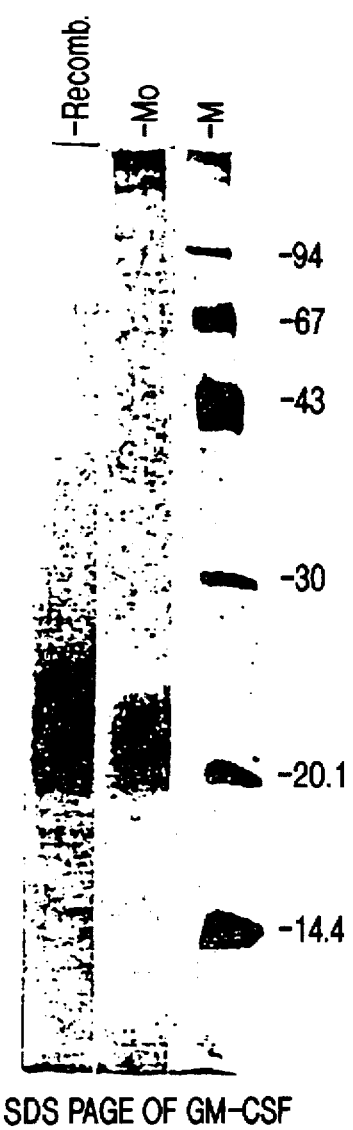
FIG. 2 illustrates SDS-PAGE analysis of the purified CSF protein.

Colony-stimulating factor activity (CSF) can be derived from a number of cellular sources including conditioned medium from peripheral blood mononuclear cells, lung and placental tissue, and bone marrow, urine from anemic patients, serum, and normal and nonplastic cells of T-lymphocyte and mononuclear phagocyte lineage. One cell line that produces CSF is the Mo cell line. The CSF produced by this cell line is known as granulocyte-macrophage CSF (or GM-CSF).

CSFs can also be produced using recombinant DNA techniques to clone CSF/cDNA and DNA that expresses CSF can be transfected into suitable host cells for expression of CSF protein. See copending U.S. Ser. No. 623,342 filed Jul. 6, 1984, which is hereby incorporated by reference.

CSFs from any source can be purified by the process of the present invention. The conditioned medium from any source of CSF protein is preferably concentrated by ultra-filtration to a protein concentration of at least about 0.1 mg protein per ml. The protein is then precipitated by adding ammonium sulfate to 80% of saturation. The resulting pellet is resuspended in an aqueous solution buffered at a pH in the range of about 6 to about 8. Examples of suitable buffers include Tris-HCl HEPES, sodium citrate, and the like.

The buffered solution is fractionated by column chromatography. Suitable materials for use in the chromatography; column are octylsepharose, DEAE-ultrogel, AcA44-ultrogel, and the like. One or more of these materials can be used in sequence to obtain higher purity.

Fractions from each column are collected and assayed for CSF activity. The active fractions are pooled and diluted with trifluoroacetic acid (TFA), heptafluorobutyric acid (HFBA), or the like, and applied to a C4 reverse phase column. The CSF activity is then eluted using a 0–90% acetonitrile gradient in TFA or HFBA, preferably at a concentration of 0.10% or 0.15% (vol/vol) respectively, depending upon which acid was used to apply the pooled fractions to the column.

The fractions having CSF activity are analyzed by SDS polyacrylamide gel electrophoresis (13.5% gel as described by Lammli, U. Nature 227, 680 (1970)). Additional treatments using the above mentioned chromatographic column materials can further purify the CSF protein to homogeneity.

Purified CSF protein fractionated by SDS-PAGE revealed a heterogeneous CSF protein having an apparent molecular weight in the range of about 15,000 to about 26,000 daltons. This apparent size heterogeneity is due to the extensive glycosylation of the protein and is a common feature of glycoproteins. Fractionation of less purified samples from Mo cell conditioned medium by SDS-PAGE (under non-reducing conditions) and assaying protein eluted from the gel revealed the[0a ]resence of a second protein having CSF activity having an apparent molecular weight of about 28,000 to 30,000.

CSF activity binds and elutes from octylsepharose, DEAE ultragel and the C4 reverse phase column. Roughly 60% of the CSF activity binds a Con-A sepharose (40% flow through) and can be eluted with alpha methylmannoside. Molecular weight analysis of recombinant CSF by gel filtration in low salt revealed that about 30% of the activity eluted with an estimated molecular weight of about 19,000 but 70% of the material behaved as dimers, eluting at a position corresponding to a molecular weight of about 38,000. If 1M NaCl is included in this column, all of the activity elutes in a broad peak at about 19,000 daltons.

The purified CSF is stable for at least 16 hours when incubated at 4° C. (pH 7.4) in 4M guanidine hydrochloride; in 10 mM EDTA; 10 mM 2-mercaptoethanol; and in 30% (v/v) ethanol. The CSF activity also is stable in 0.1% trifluroacetic acid (TFAI (pH 2.0) and 0.1% TFA plus 25% (v/v) acetonitrile.

As aforesaid, the CSF protein in accord with the present invention can be used for treatment of myelo-suppression such as (symptomatic) granulocytopenia. For such use, a daily dosage of about 200 to 1000 ug per patient is typically indicated. The CSF protein is preferably injected into the patient intravenously in a suitable pharmacological carrier. Examples of such carriers include pharmacological saline and human serum albumin in saline.

The invention will be further understood with reference to the following illustrative embodiments, which are purely exemplary, and should not be taken as limitive of the true scope of the present invention, as described in the claims. In the examples, unless otherwise specified, temperatures are in ° C. and percents are generally weight/volume percent. All steps in the purification with the exception of the reverse phase HPLC columns are performed at 0–4° C. The reverse phase HPLC is performed at room temperature.

Example A

Step 1. Mo Cell lrine Cultures

Mo cells (ATCC CRL 8066) were grown routinely in Alpha (6% $CO_2$) or Iscove's (10% $CO_2$) medium containing 20% Fetal Calf Serum (FCS), 2mM glutamine, 100 U/ml streptomycin and 100 Uc./ml penicillin. The cells should be subcultured every 4–5 days. Cells are counted and seeded into Falcon T-175 flasks in 100–150) ml medium at density of 3–4×$10^5$ cells/ml. Cells will double in 20% FCS every 4–7 days. Growth rate is not constant and cells may sometimes appear to stop growing then go through bursts of growths Mo cells can be grown in serum-free medium. Survival is much better when cells are not washed when transferred from FCS to serum-free medium. Optimal density in Serum-Free medium (SF) is 5×$10^5$ cells/ml. Cells will grow slightly (or at least maintain constant number) for 3days in serum-free medium, and then should be fed 20% FCS for at least 4 days. This growth schedule (3 days SF, 4 days 20% FCS) can be repeated weekly if SF medium is required, with no apparent harm to the cells for several months.

Step 2. Assays for CSF Activity

A. Bone Marrow Assay

Obtain fresh bone marrow. Break apart spicules by drawing through 20, 22, then 25 gauge needle. Dilute 1:1 with sterile phosphate-buffered saline (PBS) (room temperature) and layer over Ficoll-Paque (about 30 mil BM-PBS over 6 ml Ficoll). Centrifuge at 1500 rpm for 40 minutes at room temperature. Remove fat and PBS layer and discard. Pipette off the light density layer. Wash twice (2×) with PBS and count. Plate cells in RPMI (purchased from GIBCO as RPMI 1640) plus 10% heat inactivated FCS (HIFCS) for 3 hours to remove adherent cells.

Plating medium (make fresh):

20% FCS 0.3% agar dissolved in $H_2O$ cooled to 40° C.

2×Iscoves (1:1 v/v with Agar)

Final concentration of 100 U/ml penicillin, 100 ug/ml streptomycin $10^{-4}$M alpha thioglycerol in 2×Iscoves from $10^{-2}$M stock Cool agar to about 40°. Mix with other ingredients.

Cool in $H_2O$ bath to 37°–38° and hold at that temperature.

After 3 hours, pipette off the non-adherent cells. Spin arid count. Add 2×$10^5$ cells/ml of plating medium and keep in controlled temperature water bath at 37°–38°. Add samples (e.g., medium from transfected cells; usually 10 ul sample)

to the first row of wells of a microtiter plate in duplicates If the sample is not sterile, it should be filtered. This is readily done by adding bovine serum albumin to a final concentration of 0.1 mg/ml then centrifuging the sample through nitrocellulose filters having 0.2 micron pore size using the Schleicher and Schuell microfiltration centrifuge tubes. Add 100 ul cell suspension to each well. Add additional 50 ul of cell suspension to each well in the first row. Mix thoroughly and transfer 50 ul of solution from the first row into the next row, etc. and continue 1:3 dilutions across plate. Wrap the plate in parafilm. Incubate 10-14 days at 10% $CO_2$, 37° C. in fully humidified atmosphere and score colonies.

To score the colonies, the total number of colonies that grow in each well is counted. In each assay, several wells are plated without including a sample (blank) to obtain a background colony count. The average number of colonies that grow in the blank wells is subtracted from the number of colonies found in each of the wells containing samples. One unit of CSF is the amount that will stimulate the formation of one colony above the background level per $10^5$ human bone marrow cells (plated at $10^5$ cells per ml) when the CSF concentration is sub-saturating. The sub-saturating concentration is determined by dilution and comparing the number of colonies at; various dilutions to fond the concentration just below the saturation level.

For this assay, the colonies containing granulocytes, monocytes or both types of cells are counted. The types of cells in the colonies are determined by picking colonies and staining individual cells.

B. KG-1 Cell Assay

KG-1 cells (Blood, Vol. 56, No. 3 (1980)) are grown in Iscoves medium+10% FCS passed 2×per week and seeded for each passage at $2 \times 10^5$ cells/ml. The cells are used for assay only between passage 30–35. The assay is the same as for bone marrow as described above, except the KG-1 cells are plated in agar fixture at $4 \times 10^3$ cells/ml.

The number of colonies growing in each well is determined and the background count is subtracted as in the Bone Marrow assay described above. One KG-1 CSF unit/ml is that concentration of CSF that will stimulate half of the maximum number (saturation) of KG-1 colonies to grow. The maximum number, is obtained by including a saturating level of CSF in several wells. The KG-1 assay is convenient for routinely measuring CSF activity but the results must be ultimately confirmed using the bone marrow assay and activity results are generally reported from this latter assay system.

Step 3. Purification of CSF from Mo Cell Line

Mo serum free conditioned medium (40 liters was incubated at 55° C. for 30 minutes to inactivate the HTLV-II virus associated with the cell line. This medium was concentrated by pressurized ultrafiltration using the Pellicon Casette with membrane PTGC (1.5 square feet) which has a 10,000 molecular weight cut-off. The protein was further concentrated by ammonium sulfate precipitation (80% saturation) The final protein pellet (800 mg) was resuspended in 100 ml of 20 mM tris(hydroxymethyl) aminomethane hydrochloride (Tris-HCi), pH 7.4, and dialyzed against the same buffer (3 times with 4 liter changes each time). The dialyzed protein was applied to a 2.5×10 cm column of DEAE (diethylaminoethyl)-ultrogel equilibrated in the same buffer. The column was washed with 800 ml of 20 mM Tris-HCl, pDH 7.4, then the CSF activity eluted with 800 ml of 20 mM Tris-HCl, pH 7.4, containing 0.12M NaCl. 10 ml fractions were collected and assayed for CSF. The active fractions (3) were pooled, and concentrated 6 fold (to 5 ml) by pressurized ultrafiltration (Amicon YM5 membrane, 5,000 molecular weight cut-off). The concentrated sample from the DEAE column was applied to a 1.6×100 cm AcA44 ultrogel (an acrylamide agarose ultrogel having 10 to 130 k Dalton fractionation) column equilibrated in 20 mM N-2-hydroxyethylpiperazine-N-2-ethane sulfonic acid (HEPES), pH 7.4, 50 mM NaCl, and 0.01% polyethylene glycol (PEG-8000). CSF activity eluted from the column with an apparent molecular weight of 30 k Daltons. The active fractions were pooled and brought to 0.15% (v/v) trifluoroacetic acid (TFA) by addition of 10% TPA and applied to a Vydac $C_4$ reverse phase column (1×2.5 cm). The column was developed with a linear gradient of 0–90% acetonitrile in 0.1% TFA (v/v) at 4 ml/min (1,000 ml total). The CSF activity eluted at approximately 47% (v/v) acetonitrile. The pooled active fractions were brought to 0.05% (v/v) heptafluorobutyric acid (HFBA) by addition of one half volume of 0.15% (v/v) HEBA and applied to a Vydac $C_4$ column (0.46×25 cm) equilibrated in 0.15% (v/v) HFBA. The column was developed with a linear gradient of 0–90% (v/v)- acetonitrile in 0.15% (v/v) HFBA at 1 ml/min. (340 ml total). The CSF activity eluted at about 53% (v/v) acetonitrile. Fractions 37–44 (1 ml each) were found to be active. 0.15 ml of fraction 40 was concentrated 4 fold (using the SAVANT Speed Vac Concentrator) and 40 ul of 2×SDS gel sample buffer aided (0.125 M Tris- HCl, pH 6.8, 4% SDS, 20% glycerol and 0.004% Bromophenol blue). These samples were boiled for 2 minutes and applied to a 13.5% Lammli, U. Nature 227, 680 (1970) SDS gel (See FIG. 2). Fraction (#40) was determined to have 110,000 bone marrow CSF units/ml. This corresponds to about $3.0 \times 10^7$ units per $A_{280}$ absorbance unit. Since typical proteins have extinction. coefficients ranging between 0.8 and 1.2 $A_{280}$ unit per milligram, the purified CSF had a specific activity in the range of about $1 \times 10^7$ to about $4 \times 10^7$ units per mg in the bone marrow assay. A 1 ug sample of purified GM-CSF was submitted to Edman Degradation using the Applied Biosystems Gas Phase Microsequenator. The sequence of residues 3 through 5 was determined to be Ala Arg

EXAMPLE B

Step 1. M6 Cos Cell Transfection

M6 COS Monkey cells were grown routinely in Dulbecco's Modified Eagle's Medium (DME available from Gibco) containing 10% heat inactivated (55° for 30 minutes) fetal calf serum (HIFCS). The cells are split 1:6, twice a week. Twenty four hours prior to transfection, $1.2 \times 10^8$ M6 cells (split 1:6) are seeded into a Cell Factory (available from Nunc) in 1.5 liters of DME+10% HIFCS. Immediately before transfection, the medium is aspirated from the cell factory and the cells are washed twice with serum free DME (SF DME).

Plasmid DNA, a CDNA encoding human CSF (as illustrated in FIG. 1) inserted into the eukaryotic expression vector p91023(B) (p091023(B)-CSF) is purified from 2 liters of bacteria by equilibrium density centrifugation in CsCl and ethidium bromide. Details of the construction of vector p91023(B) can be found in copending Ser. No. 628,342. One mg of this DNA was dissolved in 1 ml of 0.1M Tris, pH 7.3 and added to 600 ml of DME containing 2 mM glutamine, 100 U/mi streptomycin, 100 ug/ml penicillin (P/S) and 0.25 mg/ml DEAE Dextran (Molecular weight 500,000 from Pharmacia). The 600 ml of DNA DEAE Dextran solution is added to the M6 COS cells in the cell factory and incubated at 37° for 12 hours. After the incubation, the cells are rinsed once with 900 ml of SF DME then incubated for 2.5 hours with 600 ml of DME containing 0.1 mM chloroquin, 10% HIFCS, 2 mM glutamine, 100 U/ml penicillin and 100 ug/ml streptomycin. After aspirating the chloroquin containing medium, the cells are rinsed with SF DME and fed 1500 ml of DME with 10% HIFCS. After 30 hours the cells are washed with SF DME, the medium is replaced with 800 ml of SF DME and the transfected cells are allowed to condition the medium for 24 hours at 37° C. The conditioned medium is aspirated and replaced with another 800 mil of SF DME. The cells are allowed ton condition this medium or 24 hours then the conditioned medium is. collected. As soon as possible after harvesting, the conditioned, media sample are concentrated 20 fold by pressurized ultrafiltration using the Amicon 2.5 liter chamber with the YM5 membrane (5,000 MW cutoff).

Step 2. Purification of Recombinant CSF

Two hundred ml of concentrated conditioned medium (from 4 liters of starting material) was brought to 30% saturation of ammonium sulfate by addition of solid ammonium sulfate and the precipitated protein was removed by centrifugation. The supernatant was brought to 80% saturation of ammonium sulfate by adding more solid ammonium sulfate and the precipitated protein collected by centrifugation. The pellet was resuspended in 5 ml of 20 mM sodium citrate, pH 6.1, containing 1M NaCl. The dissolved protein was applied to a 1.6×100 cm column of Ultrogel AcA54 (acrylamide agarose ultrogel having 5 to 70 k dalton fractionation) equilibrated in the same buffer. The CSF activity eluted from the column with an apparent molecular weight of about 19 k Daltons or after about 90 ml. It has been observed that if the gel filtration is performed at low ionic strength, CSF activity is eluted from the column in two positions with apparent molecular weights of about 19 k Daltons and about 38 k Daltons, suggesting that GM-CSF may readily form dimers.) The active fractions were pooled and brought to 0.15% TFA (by addition of 10% (v/v) TFA) and applied to a Vydac C4 column (0.46 ×25 cm) equilibrated in 0.1% TFA. The column was developed with a linear gradient of 0–90% (v/v) acetonitrile (1 ml/min., 340 ml total) in 0.1% TFA. The CSF activity eluted between 39 and 43% acetonitrile (Fractions 16–20). A 20 ul sample of Fraction was analyzed by SDS polyacrylamide gel electrophoresis (13.5% gel as described by Lammli, op. cit). A single broad protein band with an apparent range of 18 to 26 k Daltons was observed, again consistent with the extensive glycosylate of the CSF protein (FIG. 2). Protein from Fraction 19 was submitted to Edman Degradation using the Applied Biosystems gas phase microsequenator. From approximately 20 ug of protein applied, the sequence of the first 16 amino acids was obtained (A-P-A-R-S-P-S-P-S-T-Q-P-W-E-H). The high yield of this single sequence strongly suggests that the CSF protein in Fraction 19 had been purified to homogeneity.

Bioassay indicated that the Fraction 19 CSF had $3 \times 10^7$ units per $A_{280}$ absorbance unit in the bone marrow assay. Since typical proteins in aqueous solution exhibit a range of extinction coefficients of 0.8 to 1.2 $A_{280}$ absorbance units per milligram, the specific activity of the purified CSF is between about $1 \times 10^7$ and about $4 \times 10^7$ units/mg when assayed using the human bone marrow cell assay.

This invention has been described in detail, including the preferred embodiments thereof. However, it will be appreciated that those skilled in the art, upon consideration of this specification, may make modifications and improvements within the spirit and scope of the invention.

For instance, it has been shown that murine CSFs activate neutrophils. Thus, it would be expected that the primate CSFs of the present invention will also activate neutrophils. Therefore physiological functions of CSF may be severalfold. In the bone marrow, this lymphokine can stimulate proliferation and differentiation of effector cells for host defense while, in the periphery, new and existing cells can be activated. In a localized immunological response CSF can retain circulating neutrophils in or away from areas of inflammation. Inappropriate localization and/or activation of neutrophils can be involved in the pathophysiology of a variety of immune-mediated disorders such as rheumatoid arthritis.

What is claimed is:

1. A method of treating a patient having an infectious disease, comprising the steps of:
    selecting a pharmaceutical composition comprising substantially purified human GM-CSF and a pharmaceutically acceptable carrier; and
    administering said pharmaceutical composition to a human in need thereof.

2. The method of claim 1, wherein administering said pharmaceutical composition activates or increases the number of myeloid cells of the human.

3. The method of claim 2, wherein administering said pharmaceutical composition activates or increases the number of neutrophils, granulocytes or monocytes.

4. The method of claim 1, wherein said pharmaceutically acceptable carrier comprises pharmacological human serum albumin and saline.

5. The method of claim 1 or 4, wherein said composition is injected into the human at a daily dosage of 200 to 1000 µg per patient.

6. The method according to claim 5, comprising the additional step of selecting as said pharmaceutical composition a composition having an activity of at least about 10 million units per mg in a bone marrow assay.

* * * * *

UNITED STATES PATENT AND TRADEMARK OFFICE
CERTIFICATE OF CORRECTION

PATENT NO. : 5,795,568

DATED : August 18, 1998

INVENTOR(S) : ELIZABETH A. WANG

Page 1 of 4

It is certified that error appears in the above-identified patent and that said Letters Patent is hereby corrected as shown below:

Title page, item [57], line 6,

"columns" should read --column,--.

COLUMN 1

Line 4, "Ser. No. 08/344,806," should read --Ser. No. 08/344,809--.
Line 14, "19, 1994," should read --19, 1984,--;
Line 31, "For" should read --for--;
Line 35, "n" should read --in--;
Line 53, "I" should be deleted; and
Line 57, "step-(Burgess, A." should read --step (Burgess, A.--

COLUMN 2

Line 4, "CSFS." should read --CSFs.--;
Line 8, "W. r" should read --W,--;
Line 11, "myelo-suppress-on" should read --myelo-suppression--;
Line 14, "and or" should read --and/or--;
Line 21, "proteins" (first occurrence) should read --protein--;
Line 25, "The" should read --¶ The--;
Line 28, "However" should read --However,--;
Line 36, "accord" should read --accordance--;
Line 40, "accord" should read --accordance--;
Line 41, "purifying," should read --purifying--; and
Line 54, "(sympotomatic)" should read --(symptomatic)--.

UNITED STATES PATENT AND TRADEMARK OFFICE
CERTIFICATE OF CORRECTION

PATENT NO. : 5,795,568

DATED : August 18, 1998

INVENTOR(S) : ELIZABETH A. WANG

It is certified that error appears in the above-identified patent and that said Letters Patent is hereby corrected as shown below:

COLUMN 3

Line 3, "nonplastic" should read --neoplastic--;
    Line 11, "U.S. Ser. No. 623,342" should read
        --U.S. Ser. No. 628,342--;
    Line 21, "Tris-HC1" should read --Tris-HCl,--;
    Line 23, "chromatography;" should read --chromatography--;
    Line 33, "(vol/vol)" should read --(vol/vol),--;
    Line 39, "above mentioned" should read --above-mentioned--;
    Line 49, "the [0a]resence" should read --the presence--
        and close up right margin; and
    Line 53, "ultragel" should read --ultrogel--.

COLUMN 4

Line 1, "(TFAI" should read --(TFA)--;
    Line 3, "accord" should read --accordance--;
    Line 21, "Irine" should read --Line--;
    Line 25, "100 Uc,/ml" should read --100 $\mu$g/ml--;
    Line 27, "100-150) ml" should read --100-150 ml--;
    Line 31, "growths" should read --growth.--;
    Line 37, "3days" should read --3 days--;
    Line 47, "30 mil" should read --30 ml--; and
    Line 64, "arid" should read --and--.

UNITED STATES PATENT AND TRADEMARK OFFICE
CERTIFICATE OF CORRECTION

PATENT NO. : 5,795,568

DATED : August 18, 1998

INVENTOR(S) : ELIZABETH A. WANG

It is certified that error appears in the above-identified patent and that said Letters Patent is hereby corrected as shown below:

COLUMN 5

```
Line 1,  "duplicates" should read --duplicate.--;
Line 24, "at;" should read --at-- and "fond"
         should read --find--;
Line 42, "number," should read --number--;
Line 49, "serumfree" should read --serum-free--
         and "(40 liters" should read --(40 liters)--;
Line 56, "saturation)" should read --saturation).--;
Line 58, "(Tris-HCi)," should read --(Tris-HCl),--; and
Line 63, "pDH 7.4," should read --pH 7.4,--.
```

COLUMN 6

```
Line 10, "TPA" should read --TFA-- and "(1x2.5" should
         read --(1x25--;
Line 16, "HEBA" should read --HFBA--;
Line 19, "(v/v)-acetonitrile" should read
         --(v/v) acetonitrile--;
Line 24, "Tris- HCl," should read --Tris-HCl,--;
Line 31, "tion." should read --tion--;
Line 37, "Ala Arg" should read --Ala Arg Ser.--;
Line 45, "Twenty four" should read --Twenty-four--;
Line 49, "serum free" should read --serum-free--;
Line 51, "CDNA" should read --cDNA--;
Line 53, "(p091023(B)-CSF)" should read
         --(p91023(B)-CSF)--; and
Line 59, "100 U/mi" should read --100 U/ml--.
```

UNITED STATES PATENT AND TRADEMARK OFFICE
CERTIFICATE OF CORRECTION

PATENT NO. : 5,795,568

DATED      : August 18, 1998

INVENTOR(S) : ELIZABETH A. WANG

It is certified that error appears in the above-identified patent and that said Letters Patent is hereby corrected as shown below:

COLUMN 7

Line 7, "800 mil" should read --800 ml-- and "ton" should read --to--;
    Line 8, "or" should read --for--;
    Line 9, "is." should read --is--;
    Line 10, "conditioned," should read --conditioned--; and
    Line 39, "Fraction" should be deleted.

COLUMN 8

Line 15, "Therefore" should read --Therefore,--.

Signed and Sealed this

Thirteenth Day of April, 1999

Attest:

Attesting Officer

Q. TODD DICKINSON

Acting Commissioner of Patents and Trademarks